US009421084B2

(12) United States Patent
Barker

(10) Patent No.: US 9,421,084 B2
(45) Date of Patent: Aug. 23, 2016

(54) STENT

(75) Inventor: Stephen Edward George Barker, London (GB)

(73) Assignee: Newtec Vascular Products Limited, Liverpool (GB)

(*) Notice: Subject to any disclaimer, the term of this patent is extended or adjusted under 35 U.S.C. 154(b) by 905 days.

(21) Appl. No.: 13/021,162

(22) Filed: Feb. 4, 2011

(65) Prior Publication Data
US 2011/0172761 A1 Jul. 14, 2011

Related U.S. Application Data

(63) Continuation of application No. 11/995,915, filed as application No. PCT/GB2006/002775 on Jul. 24, 2006.

(30) Foreign Application Priority Data

Jul. 22, 2005 (GB) .................................. 0515140.2

(51) Int. Cl.
 A61B 17/11 (2006.01)
 A61F 2/06 (2013.01)
 A61F 2/30 (2006.01)

(52) U.S. Cl.
 CPC .............. *A61F 2/064* (2013.01); *A61B 17/11* (2013.01); *A61B 2017/1107* (2013.01); *A61B 2017/1132* (2013.01); *A61B 2017/1135* (2013.01); *A61F 2002/30062* (2013.01); *A61F 2210/0004* (2013.01)

(58) Field of Classification Search
 CPC ............ A61B 2017/1132; A61B 2017/1135
 USPC ..................... 623/1.35, 1.36; 604/8
 See application file for complete search history.

(56) References Cited

U.S. PATENT DOCUMENTS

| 3,626,947 | A | 12/1971 | Sparks |
| 4,743,251 | A | 5/1988 | Barra |
| 5,152,782 | A | 10/1992 | Kowligi et al. |
| 5,620,409 | A * | 4/1997 | Venuto ............ A61B 17/22004 601/2 |
| 6,071,306 | A | 6/2000 | Angelini |
| 6,210,430 | B1 * | 4/2001 | Solem ................. A61B 17/11 623/1.11 |
| 6,355,055 | B1 * | 3/2002 | Waksman et al. ............ 623/1.13 |
| 6,743,243 | B1 | 6/2004 | Roy et al. |
| 7,060,684 | B1 * | 6/2006 | Quijano et al. ............ 604/891.1 |
| 7,998,188 | B2 * | 8/2011 | Zilla ........................ A61F 2/06 623/1.13 |
| 2004/0068278 | A1 | 4/2004 | Fleischman et al. |
| 2005/0038498 | A1 * | 2/2005 | Dubrow et al. .............. 623/1.15 |
| 2005/0043752 | A1 | 2/2005 | Phan et al. |
| 2005/0171565 | A1 | 8/2005 | Yencho et al. |
| 2006/0030869 | A1 * | 2/2006 | Loshakove ....... A61B 17/00491 606/153 |
| 2006/0149360 | A1 | 7/2006 | Schwammenthal et al. |
| 2008/0208323 | A1 * | 8/2008 | El-Kurdi .................. A61F 2/06 623/1.36 |

(Continued)

FOREIGN PATENT DOCUMENTS

| JP | 4-505720 | 10/1992 |
| WO | WO 98/20027 | 5/1998 |

*Primary Examiner* — Christian Sevilla
*Assistant Examiner* — Seema Mathew
(74) *Attorney, Agent, or Firm* — Saliwanchik, Lloyd & Eisenschenk

(57) ABSTRACT

An elongate device, actuate in cross-section, for placement around a vessel, comprises an essentially non-porous outer layer and a biodegradable inner layer.

Figure 1:
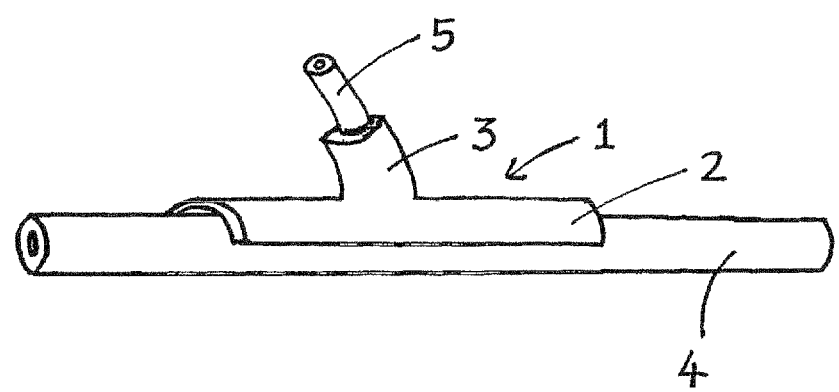

An alternative device comprises a tubular portion for placement around a graft and a portion, arcuate in cross-section, that can straddle a native vessel, at the site of an end-to-side anastomosis.

13 Claims, 1 Drawing Sheet

(56) References Cited

U.S. PATENT DOCUMENTS

| | | | |
|---|---|---|---|
| 2011/0230955 A1* | 9/2011 | Orion | A61F 2/82 623/1.15 |
| 2014/0005586 A1* | 1/2014 | Feinstein | A61F 2/958 604/8 |
| 2016/0143754 A1* | 5/2016 | Orion | A61F 2/064 623/1.15 |

* cited by examiner

STENT

CROSS-REFERENCE TO RELATED APPLICATIONS

This application is a continuation application of co-pending application Ser. No. 11/995,915, filed Jan. 16, 2008; which is a National Stage Application of International Application Number PCT/GB2006/002775, filed Jul. 24, 2006; which claims priority to Great Britain Application No. 0515140.2, filed Jul. 22, 2005; all of which are incorporated herein by reference in their entireties.

FIELD OF THE INVENTION

This invention relates to a therapeutic device, sometimes described herein as an external (vascular) stent, and to its use.

BACKGROUND TO THE INVENTION

Neo-intimal hyperplasia represents an increase in the number of smooth muscle cells (SMC's) between the endothelium and the internal elastic lamina of a blood vessel. When intimal hyperplasia occurs, de novo thickening of the intimal layer, or vessel wall may result, causing the vessel to become stenosed, or occluded. Proliferation of arterial SMC's commonly occurs when a blood vessel is deformed, or disturbed during surgery. Surgical anastomoses, in particular with bypass grafts (in which a vein or synthetic substitute is anastomosed to an artery), may result in SMC proliferation and, consequently, stenosis.

When an obstruction in a blood vessel has been cleared, intimal hyperplasia occurring after such intervention may lead to the vessel's becoming occluded again. This is known as re-stenosis and may require further intervention.

Atherosclerotic cardiovascular disease is the leading cause of death in Europe and North America and is caused by occlusion of the arterial lumen, either preventing, or reducing blood flow. Depending on site and disease distribution, several options for treatment exist, with arterial bypass grafting being common.

A significant number of arterial bypass grafts fail, i.e. become occluded, in the first two years following surgery. In these cases, it is SMC intimal hyperplasia that often is responsible for causing stenosis of the arterial lumen, eventually resulting in complete occlusion. SMC intimal hyperplasia occurs most commonly around the more distal anastomosis and in the "native" vessel wall opposite the anastomosis. SMC intimal hyperplasia can occur at the proximal arterial anastomosis also and along parts of the graft itself.

A graft is commonly anastomosed to the native vessel in one of three ways: "end-to-end", "end-to-side", or "side-to-side". Of these techniques, end-to-side and side-to-side are more common than end-to-end.

U.S. Pat. No. 3,626,947 describes a method and apparatus for applying a textile mesh reinforcing tube around a vein or artery. U.S. Pat. No. 4,743,251 describes a perforated flexible sheath for use in coronary bypass procedures.

EP-A-0730849 (and GB-A-2298577) disclose a non-restrictive, porous stent for use in arteriovenous bypass grafting procedures. The porous stent, when placed around a bypass vein segment, has beneficial effects on the luminal size and degree of medial and intimal thickening of the anastomosed vessel. It is apparently essential that the inner diameter of the stent should be at least 3 mm larger than the outer diameter of the expanded vein (which can only be determined in use). This specification focuses on the problems associated with end-to-end anastomoses.

SUMMARY OF THE INVENTION

The present invention is based in part upon the realisation that devices of the type described in EP-A-0730849, may be modified for use at the site of an end-to-end, end-to-side or (as in the case of coronary) side-to-side anastomosis. Such an external stent may, surprisingly, have the beneficial effects described above, at the more complex side-to-side juncture.

According to one aspect of the invention, an external device is suitable for placement over the site of, for example, an end-to-side anastomosis. Such an external stent may be used, for example, in an arterio-venous bypass grafting procedure.

Consideration of the suitable structure of such a device is the basis of a second aspect of the present invention, i.e. a stent which is elongate and comprises two layers at least semi-circular in cross-section, there being an outer, essentially non-porous layer and an inner, biodegradable layer.

DESCRIPTION OF THE INVENTION

A device of the invention preferably comprises an arcuate body portion which, in use, straddles the native vessel, and a tubular body portion which, in use, surrounds an artery, vein or synthetic graft. The arcuate portion may describe up to 270° or more, depending on flexibility. The tubular portion is typically positioned at about the midpoint of the arcuate portion. The axis of the tubular portion typically defines an acute angle (for example, 15°, 30°, 45° or 60°) with respect to the length of the arcuate portion.

The term "end-to-side" as used herein refers to an anastomosis in which an and of the (natural or synthetic) graft vessel is grafted onto the side of the native vessel. The term "non-restrictive" as used herein refers to an external stent which allows unrestricted expansion of the graft in initial response to arterial pressure.

The term "porous" as used herein refers to the ability of the external stent to be invaded by cells and small blood cells, and may transmit fluids. An indication of porosity may be obtained by determining the water-permeability of the stent. A water-permeability test refers to the rate of flow of water through a wall of the dry stent, providing an index of the interstitial leakage rate of the wall. A suitable test is described in *Practical Considerations in Fabric Vascular Grafts*, Buxton et al, *Am. J. Surg.* 125:288-293, 1973, in which the dry prosthesis is subjected to an applied head of water at a pressure of 120 mm Hg, and the volume of water which passes through the wall per minute measured. In accordance with this test, the water permeability of the stent is preferably at least 5 ml/min/cm$^2$, e.g. about 20000 ml/min/cm$^2$. Porosity may be the consequence of treating an otherwise continuous material, and may be achieved using any suitable technique, for example needling.

The external stent may be made of any suitable material or materials, e.g. a material that is known in the art. In accordance with the second aspect of the invention, it may be preferred to use two layers of material, of which the inner may be stimulatory (for neovascularisation) and relatively fast-degrading. The degradation times may be up to 90 days. The material of the inner layer is preferably a biodegradable material such as collagen. This provides a medium for the introduction of an active agent appropriate for use in therapy, e.g. as described in WO98/20027, the content of which is incorporated herein by reference.

The outer layer may be relatively rigid, and provide a structural framework of the device. It may comprise ribbing or some other reinforcement. The outer layer may be relatively or essentially non-porous, e.g. of Dacron, PTFE, polyester or polyurethane. The two layers may be independent or they may be bound together, before use.

Depending on the extent to which the device is intended to surround the vessel, it may be self-supporting in use. For example, there may be an elongate slit, allowing the device to be opened up and placed around the vessel by a surgeon.

The two layers may provide a directional delivery system, for an active agent that is introduced or incorporated into the product. The whole may be sealed in use, e.g. using a sealant such as GAA glue.

Figure 2:
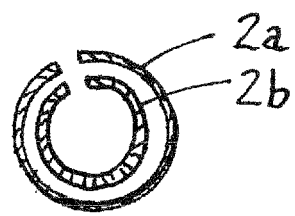

The invention will now be described, by way of example only, with reference to the accompanying drawings. FIG. 1 shows, in perspective, a schematic view of an external stent that embodies the invention positioned around the site of an "end-to-side" anastomosis. FIG. 2 is a cross-sectional view of another embodiment of the invention.

FIG. 1 shows an external stent 1 having an elongate, arcuate (in cross-section) body portion 2 and a tubular body portion 3; the two portions are joined to form (in cross-section) a generally. Y-shaped body. The arcuate body portion, in use, straddles a native blood vessel 4. The tubular portion is shown as surrounding a graft 5 anastomosed to the native vessel in end-to-side fashion. The internal diameter of the tubular body portion is preferably at least 2 mm greater than the diameter of the graft, but need be no greater. The internal diameter of the second body portion is preferably about 6 to about 8 mm. The arcuate body portion is, for example, 30 to 50 mm in length, and can be cut to size; the tubular portion may be 10 to 30 mm in length, and can be cut to length. A surgeon may advantageously have available a series of such external stents, of different sizes, angulation and shapes, from which to choose that most appropriate to any given anastomosed vessel. Fitting the stent to the vessel and graft may be achieved by first sliding the tubular portion over the end of the graft. The surgeon is then able to anastomose the free end of the graft to the native blood vessel and then slide the stent back down the graft so that it covers the site of the anastomosis. The stent may be fixed by suturing, if desired.

FIG. 2 shows a device comprising an outer layer 2a and an inner layer 2b. These layers are not continuous, and the device can be opened up, for placement about a vessel. In practice the two layers will usually be contiguous, with the respective materials' natural elasticity maintaining them in contact. Alternatively, they may be bonded together.

The relevant dimensions of the device illustrated in FIG. 1 should be considered as illustrative of each such dimension, independently. Similarly, each such dimension may be illustrative of a device of the type illustrated in FIG. 2.

I claim:

1. An arteriovenous bypass grafting procedure, which comprises fitting an elongate device around an external surface of a vessel to be grafted, wherein the device is arcuate in cross-section and self-supporting, and wherein the device comprises inner and outer layers that are maintained in contact by their natural elasticity or by bonding, wherein the outer layer is more rigid than the inner layer such that it provides a structural framework for the device, wherein the inner layer stimulates neovascularisation and degrades faster than the outer layer, and wherein the device is fitted around the external surface of the vessel such that there is a space between the device and the vessel.

2. The procedure according to claim 1, which comprises fitting the device at the site of an end-to-side anastomosis.

3. The procedure according to claim 1, wherein the device is substantially Y- or T-shaped.

4. The procedure according to claim 1, wherein the outer layer is non-porous.

5. The procedure according to claim 1, wherein the arcuate cross-section includes an angle of up to 270°.

6. The procedure according to claim 1, wherein the device is essentially tubular.

7. The procedure according to claim 6, wherein the tubular portion has an internal diameter of up to 8 mm.

8. The procedure according to claim 1, wherein the device includes an elongate slit.

9. The procedure according to claim 1, wherein the device includes an active agent.

10. The procedure according to claim 1, wherein the inner and outer layers are discrete.

11. The procedure according to claim 1, wherein the device is spaced apart from the vessel by at least 1 mm.

12. The procedure according to claim 11, wherein the inner layer is spaced apart from the vessel along the device's entire length, including at the ends of the device such that the ends of the device are open.

13. The procedure according to claim 1, wherein the inner layer is spaced apart from the vessel along the device's entire length, including at the ends of the device such that the ends of the device are open.

* * * * *